US012569208B2

(12) United States Patent
Teshigawara

(10) Patent No.: US 12,569,208 B2
(45) Date of Patent: Mar. 10, 2026

(54) PET APPARATUS, IMAGE PROCESSING METHOD, AND NON-TRANSITORY COMPUTER-READABLE STORAGE MEDIUM

(71) Applicant: CANON MEDICAL SYSTEMS CORPORATION, Tochigi (JP)

(72) Inventor: Manabu Teshigawara, Otawara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 278 days.

(21) Appl. No.: 18/306,404

(22) Filed: Apr. 25, 2023

(65) Prior Publication Data

US 2023/0337992 A1 Oct. 26, 2023

(30) Foreign Application Priority Data

Apr. 25, 2022 (JP) ................................. 2022-071900

(51) Int. Cl.
*A61B 6/03* (2006.01)
*A61B 6/42* (2024.01)
(52) U.S. Cl.
CPC ............ *A61B 6/037* (2013.01); *A61B 6/4258* (2013.01); *A61B 6/4266* (2013.01)
(58) Field of Classification Search
CPC ..... A61B 6/037; A61B 6/4258; A61B 6/4266; A61B 6/4275; A61B 6/486; A61B 6/5205; G06T 11/005; G06T 11/003; G06T 2211/40; G01T 1/2985
See application file for complete search history.

(56) References Cited

U.S. PATENT DOCUMENTS

2005/0063611 A1* 3/2005 Toki ..................... G01N 23/046
382/299
2010/0219345 A1 9/2010 Franch et al.
(Continued)

FOREIGN PATENT DOCUMENTS

JP 2019-56700 A 4/2019

OTHER PUBLICATIONS

I. J. Ahn, J. H. Kim, Y. Chang, K. Y. Jeong and J. B. Ra, "LOR-Based Reconstruction for Super-Resolved 3D PET Image on GPU," in IEEE Transactions on Nuclear Science, vol. 62, No. 3, pp. 859-868, Jun. 2015, doi: 10.1109/TNS.2015.2421908. (Year: 2015).*

(Continued)

*Primary Examiner* — Oneal R Mistry
*Assistant Examiner* — Rachel L Roberts
(74) *Attorney, Agent, or Firm* — Oblon, McClelland, Maier & Neustadt, L.L.P.

(57) ABSTRACT

A Positron Emission Tomography (PET) apparatus according to an embodiment includes processing circuitry. The processing circuitry is configured to determine a virtual detector region on the basis of a Positron Emission Tomography (PET) detector capable of detecting, in a real number coordinate system, a light emission position of an event occurring due to pair annihilation gamma rays becoming incident, a Line Of Response (LOR) defined based on the event detected by the PET detector, and the light emission position and is configured to perform a reconstruction process on the basis of the virtual detector region.

6 Claims, 7 Drawing Sheets

(56) References Cited

U.S. PATENT DOCUMENTS

| | | | |
|---|---|---|---|
| 2010/0230602 A1* | 9/2010 | Scheins | ................ G01T 1/2985 |
| | | | 250/362 |
| 2019/0086557 A1* | 3/2019 | Teshigawara | .......... A61B 6/037 |
| 2021/0199822 A1* | 7/2021 | Li | ......................... G01T 1/2002 |

OTHER PUBLICATIONS

Extended European Search Report Issued Aug. 30, 2023 in European Application 23169850.7, (submitting English translation).
Vàzquez et al. , "Parallelization of MLEM algorithm for PET reconstruction based on GPUs", IEEE, Nuclear Science Symposium and Medical Imaging Conference (NSS/MIC), XP032879960, 2014, 4 pages.

\* cited by examiner

FIG.1

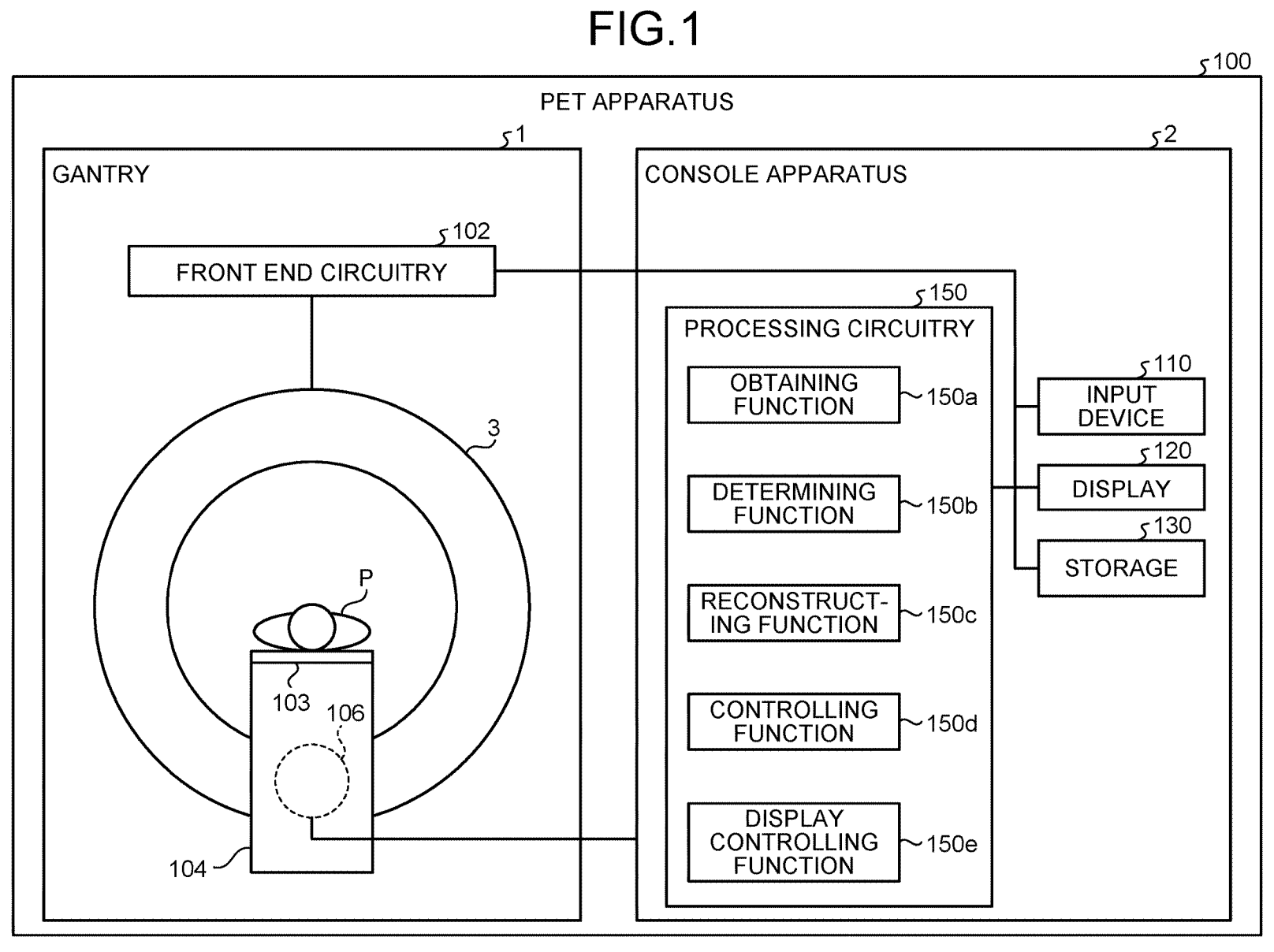

PET APPARATUS 100

GANTRY 1

FRONT END CIRCUITRY 102

P 103

106

104

3

CONSOLE APPARATUS 2

INPUT DEVICE 110

DISPLAY 120

STORAGE 130

PROCESSING CIRCUITRY 150

OBTAINING FUNCTION 150a

DETERMINING FUNCTION 150b

RECONSTRUCT-ING FUNCTION 150c

CONTROLLING FUNCTION 150d

DISPLAY CONTROLLING FUNCTION 150e

FIG.4

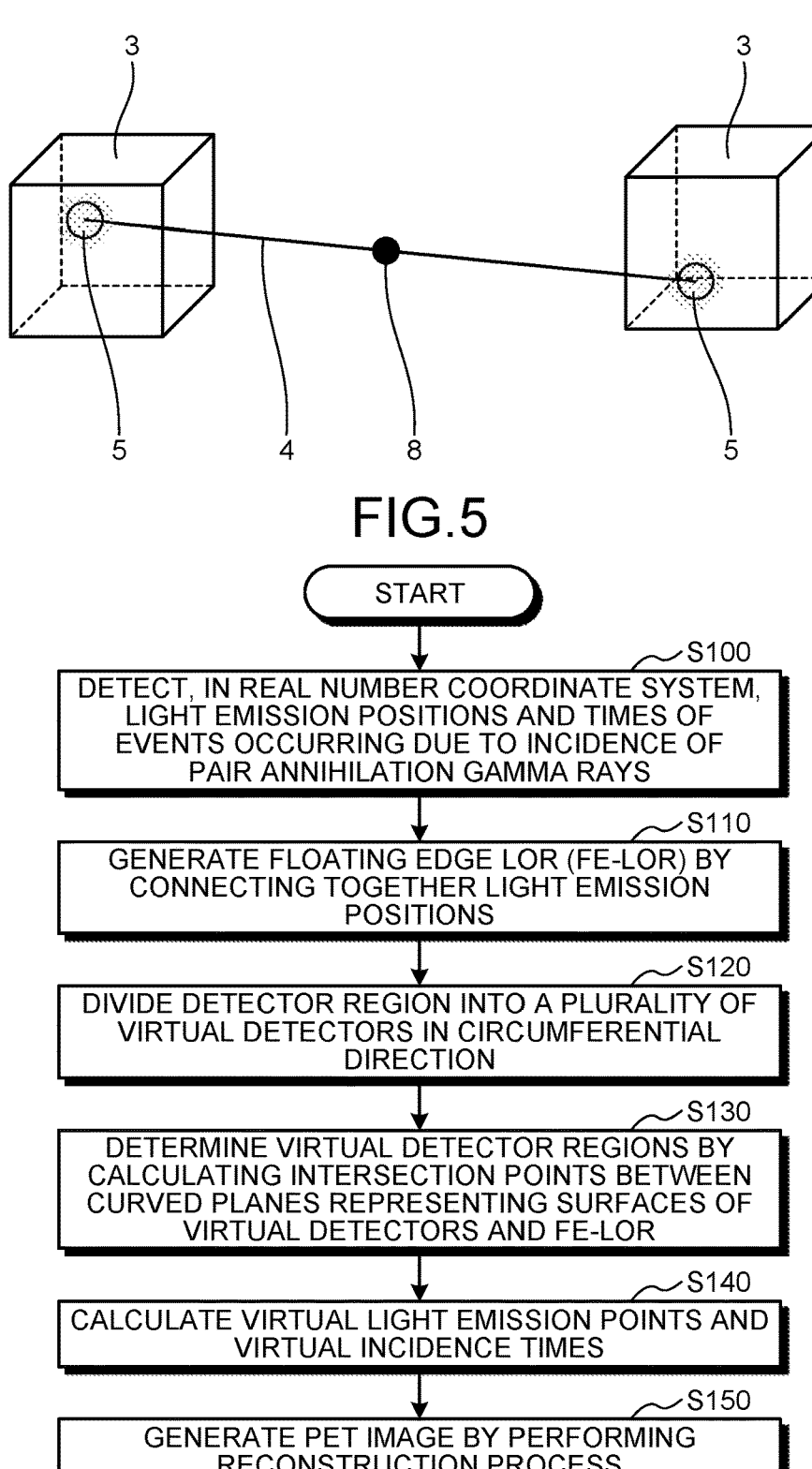

FIG.5

START

S100
DETECT, IN REAL NUMBER COORDINATE SYSTEM, LIGHT EMISSION POSITIONS AND TIMES OF EVENTS OCCURRING DUE TO INCIDENCE OF PAIR ANNIHILATION GAMMA RAYS

S110
GENERATE FLOATING EDGE LOR (FE-LOR) BY CONNECTING TOGETHER LIGHT EMISSION POSITIONS

S120
DIVIDE DETECTOR REGION INTO A PLURALITY OF VIRTUAL DETECTORS IN CIRCUMFERENTIAL DIRECTION

S130
DETERMINE VIRTUAL DETECTOR REGIONS BY CALCULATING INTERSECTION POINTS BETWEEN CURVED PLANES REPRESENTING SURFACES OF VIRTUAL DETECTORS AND FE-LOR

S140
CALCULATE VIRTUAL LIGHT EMISSION POINTS AND VIRTUAL INCIDENCE TIMES

S150
GENERATE PET IMAGE BY PERFORMING RECONSTRUCTION PROCESS

END

FIG.8

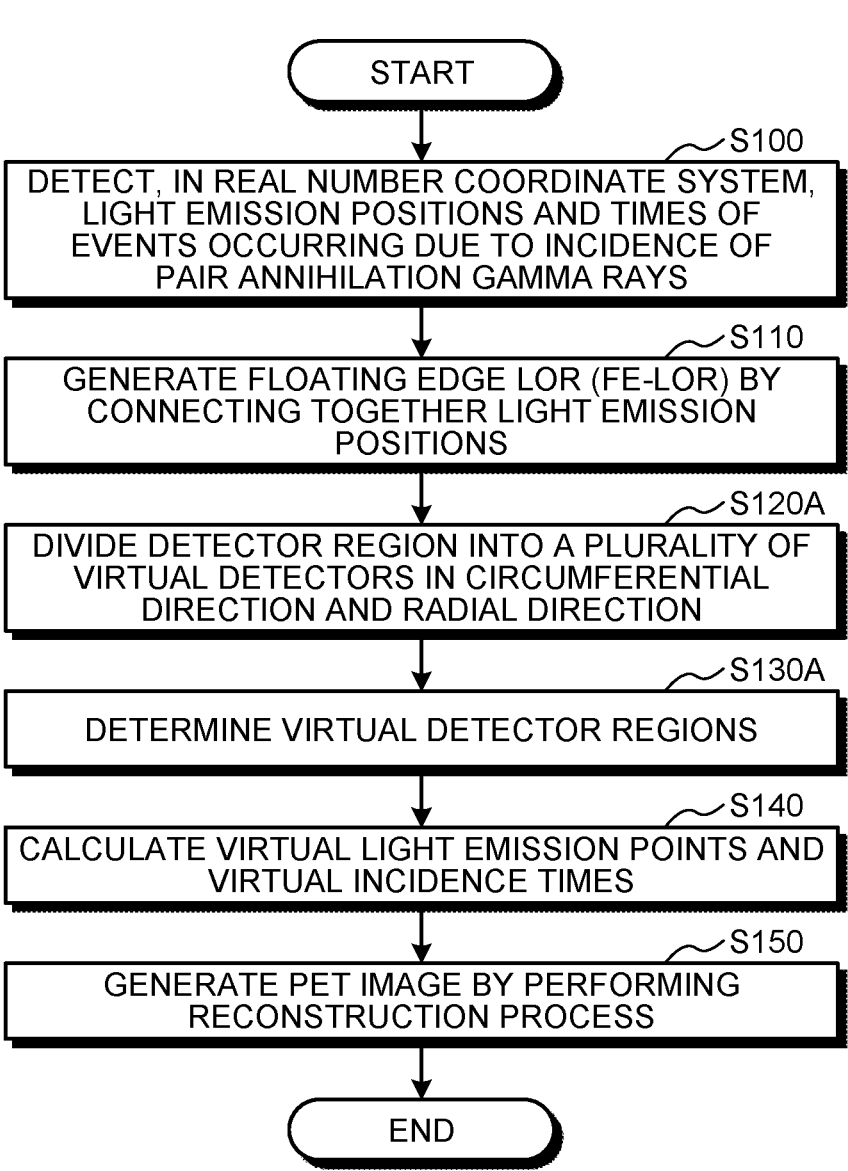

START

~S100
DETECT, IN REAL NUMBER COORDINATE SYSTEM, LIGHT EMISSION POSITIONS AND TIMES OF EVENTS OCCURRING DUE TO INCIDENCE OF PAIR ANNIHILATION GAMMA RAYS

~S110
GENERATE FLOATING EDGE LOR (FE-LOR) BY CONNECTING TOGETHER LIGHT EMISSION POSITIONS

~S120A
DIVIDE DETECTOR REGION INTO A PLURALITY OF VIRTUAL DETECTORS IN CIRCUMFERENTIAL DIRECTION AND RADIAL DIRECTION

~S130A
DETERMINE VIRTUAL DETECTOR REGIONS

~S140
CALCULATE VIRTUAL LIGHT EMISSION POINTS AND VIRTUAL INCIDENCE TIMES

~S150
GENERATE PET IMAGE BY PERFORMING RECONSTRUCTION PROCESS

END

PET APPARATUS, IMAGE PROCESSING METHOD, AND NON-TRANSITORY COMPUTER-READABLE STORAGE MEDIUM

CROSS-REFERENCE TO RELATED APPLICATIONS

This application is based upon and claims the benefit of priority from Japanese Patent Application No. 2022-071900, filed on Apr. 25, 2022; the entire contents of which are incorporated herein by reference.

FIELD

Embodiments described herein relate generally to a Positron Emission Tomography (PET) apparatus, an image processing method, and a non-transitory computer-readable storage medium.

BACKGROUND

Usually, PET apparatuses are configured to reconstruct a PET image by performing an image reconstruction on acquisition data in which light emission positions representing interactions between gamma rays and a scintillator are identified in units of scintillator pieces. Typically, each of the scintillator pieces is in the shape of a quadrangular prism, for example, of which the width and the length are each 3 mm to 4 mm, while the height is approximately 20 mm.

However, when the only way to identify the light emission positions is in units of the scintillator pieces, a theoretical limit is imposed on a spatial resolution of the PET apparatus. Further, even for light emission that occurred in a single scintillator piece, the light is actually emitted in different positions among different events. When the light emission positions are measured in units of the scintillator pieces, i.e., when the measuring process is performed without identifying the light emission point for each event within the scintillator, a theoretical limit of approximately tens of ps is caused in terms of a Time Of Flight (TOF) temporal resolution.

BRIEF DESCRIPTION OF THE DRAWINGS

FIG. 1 is a diagram illustrating an example of a PET apparatus according to an embodiment;

FIG. 4 is a drawing for explaining a detector included in the PET apparatus according to the embodiment;

FIG. 5 is a flowchart for explaining a flow in a process performed by a PET apparatus according to a first embodiment;

FIG. 8 is a flowchart for explaining a flow in a process performed by a PET apparatus according to a second embodiment.

DETAILED DESCRIPTION

Figure 2:
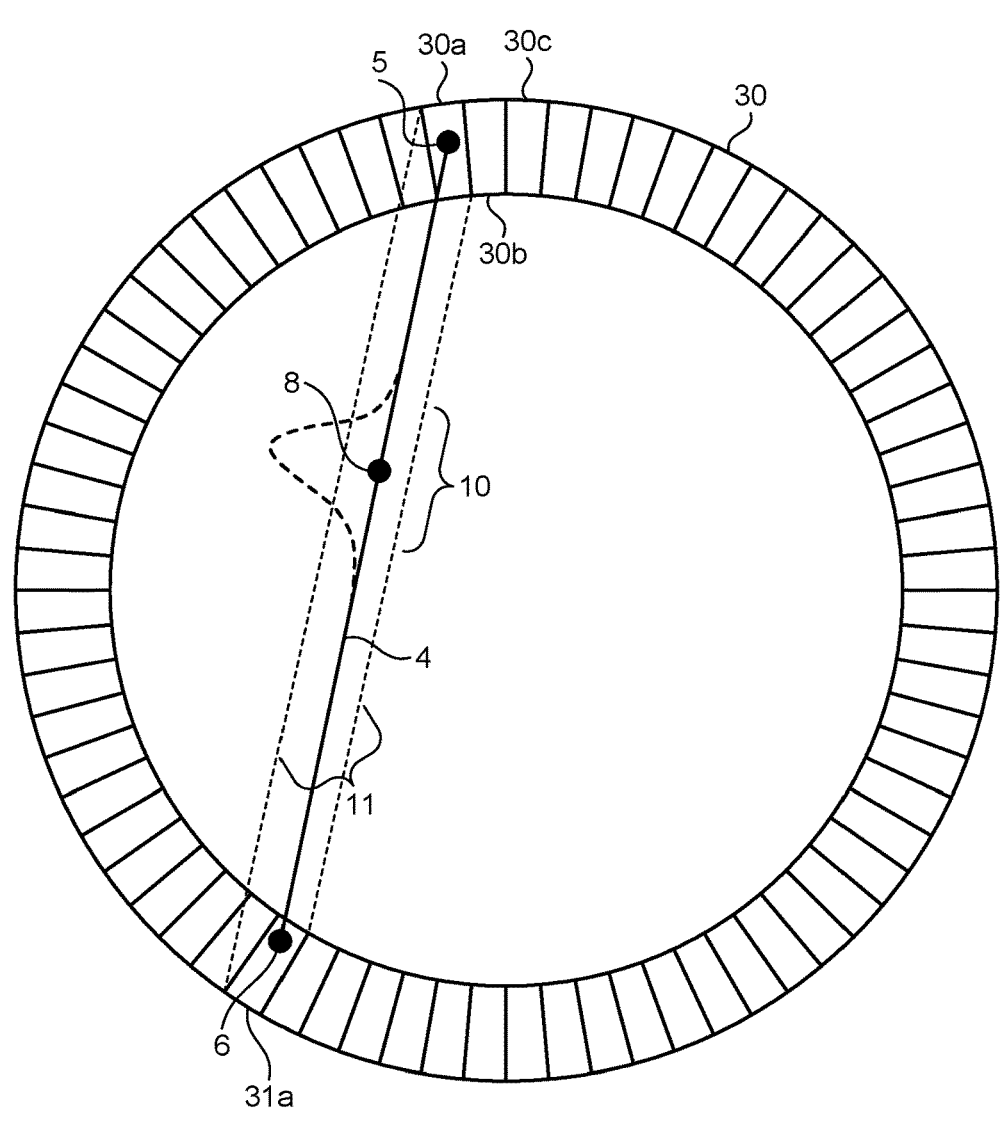
FIG. 2 is a drawing illustrating an example of a detector included in a PET apparatus according to a comparison example.

A PET apparatus provided in one aspect of the present disclosure includes processing circuitry. A virtual detector region is determined on the basis of a Positron Emission Tomography (PET) detector capable of detecting, in a real number coordinate system, a light emission position of an event occurring due to pair annihilation gamma rays becoming incident, a Line Of Response (LOR) defined based on the event detected by the PET detector, and the light emission position. A reconstruction process is performed on the basis of the virtual detector region.

Exemplary embodiments of a PET apparatus will be explained in detail below, with reference to the accompanying drawings.

First Embodiment

FIG. 1 is a diagram illustrating a configuration of a PET apparatus 100 according to an embodiment. As illustrated in FIG. 1, the PET apparatus 100 according to the embodiment includes a gantry 1 and a console apparatus 2. The gantry 1 includes a PET detector 3, front end circuitry 102, a tabletop 103, a table 104, and a table driving unit 106.

The PET detector 3 is a detector configured to detect radiation, by detecting scintillation light (fluorescent light) which is light reemitted when a substance transitions back into a ground state after being in an excited state due to an interaction between pair annihilation gamma rays and a light emitting body (a scintillator), the pair annihilation gamma rays having been generated from pair annihilation between positrons released from an imaged subject (hereinafter, "patient") P and electrons in the substance; or by detecting light emission of Cherenkov radiation or the like occurring as a result of charged particles that occurred from interactions between pair annihilation gamma rays and the PET detector 3 advancing through a medium of the PET detector 3. The PET detector 3 is configured to detect energy information of the pair annihilation gamma rays generated due to the positrons released from the inside of the patient P and information about positions (light emission positions) and times (detection times) at which the light emission occurred.

The PET detector 3 is arranged, for example, so as to surround the patient P in a ring formation and is structured with a monolithic scintillator, which is monolithic, i.e., of a single crystal.

In this situation, the monolithic scintillator is used while the single scintillator crystal is in an integral form without being separated. The scintillator is formed with the scintillator crystal suitable for TOF, such as that of Lutetium Yttrium Oxyorthosilicate (YSO), Lutetium Oxyorthosilicate (LSO), or Lutetium Gadolinium Oxyorthosilicate (LSGO), for example.

Further, possible examples of the scintillator are not limited to the examples described above. In other examples, it is possible to use, as the scintillator, Bismuth Germanium Oxide (BGO) of which the atomic number is large and which has a low absorption rate for Cherenkov radiation, or a lead compound such as lead glass ($SiO_2$+PbO), lead fluoride ($PbF_2$), or PWO ($PbWO_4$), for instance.

By employing the front end circuitry 102, the gantry 1 is configured to generate count information from an output signal of the PET detector 3 and to store the generated count information into a storage 130 of the console apparatus 2. In this situation, the front end circuitry 102 is connected to the PET detector 3.

The front end circuitry 102 is configured to generate the count information by converting the output signal of the PET detector 3 into digital data. The count information includes detection positions, energy values, and detection times of the pair annihilation gamma rays. For example, the front end circuitry 102 is configured to identify a plurality of optical detecting elements that converted scintillation light into an electrical signal with mutually the same timing. Further, the front end circuitry 102 is configured to identify positions in the scintillator at which the pair annihilation gamma rays became incident, by using continuous coordinates.

In an example, the front end circuitry 102 is configured to identify energy values (E) of the annihilation gamma rays that became incident to the PET detector 3, by performing an integral calculation on intensities of the electrical signals output from the optical detecting elements. Further, the front end circuitry 102 is configured to identify detection times (T) at which the scintillation light from the annihilation gamma rays was detected by the PET detector 3. In this situation, the detection times (T) may be absolute times or elapsed time periods since the start of an imaging process. As explained herein, the front end circuitry 102 is configured to generate the count information including the positions at which the pair annihilation gamma rays became incident, the energy values (E), and the detection times (T). Energy measurement methods that can be used by the front end circuitry 102 to identify the energy values (E) of the annihilation gamma rays are not limited to the method by which the integral calculation is performed on waveforms of the electrical signals output from the optical detecting elements. For example, it is also acceptable to use a Time Over Threshold (TOT) method by which the energy values (E) of the annihilation gamma rays are estimated with the use of a time period until a signal value returns to a specific threshold value.

Further, unlike ordinary examples in which the PET detector 3 is structured with a plurality of scintillator pieces, the monolithic scintillator is used. Thus, unlike ordinary PET apparatuses configured to obtain numbers (P) identifying scintillators to which pair annihilation gamma rays became incident, the front end circuitry 102 is able to obtain the continuous coordinate values of the positions at which the pair annihilation gamma rays became incident, as the count information.

In this situation, the front end circuitry 102 may be realized by using, for example, a Central Processing Unit (CPU), a Graphical Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)). The front end circuitry 102 is an example of a front end unit.

The tabletop 103 is a bed on which the patient P is placed and is arranged over the table 104. The table driving unit 106 is configured to move the tabletop 103 under control of a controlling function 105*d* of processing circuitry 150. For example, the table driving unit 106 is configured to move the patient P to the inside of an imaging opening of the gantry 1, by moving the tabletop 103.

The console apparatus 2 is configured to control PET image taking processes by receiving operations performed on the PET apparatus 100 by an operator and to also reconstruct a PET image by using the count information acquired by the gantry 1. As illustrated in FIG. 1, the console apparatus 2 includes the processing circuitry 150, an input device 110, a display 120, and a storage 130. In this situation, functional units of the console apparatus 2 are connected together via a bus. Details of the processing circuitry 150 will be explained later.

The input device 110 is a mouse, a keyboard, and/or the like used by the operator of the PET apparatus 100 for inputting various types of instructions and various types of settings and is configured to transfer the input various types of instructions and various types of settings to the processing circuitry 150. For example, the input device 110 may be used for inputting an instruction to start an imaging process.

The display 120 is a monitor or the like referenced by the operator and is configured, under control of the processing circuitry 150, to display a respiratory waveform and the PET image of the patient and to display a Graphical User Interface (GUI) used for receiving the various types of instructions and the various types of settings from the operator.

The storage 130 is configured to store therein various types of data used in the PET apparatus 100. For instance, the storage 130 is configured by using a memory and may be, in an example, realized by using a semiconductor memory element such as a Random Access Memory (RAM) or a flash memory, or a hard disk, an optical disk, or the like. The storage 130 is configured to store therein: the count information which is the information in which the positions in the scintillator at which the pair annihilation gamma rays became incident, the energy values (E), and the detection times (T) are kept in correspondence with one another; coincidence information in which coincidence numbers represented by serial numbers of pieces of coincidence information are kept in correspondence with sets of count information; the reconstructed PET image; and/or the like.

The processing circuitry 150 includes an obtaining function 150*a*, a determining function 150*b*, a reconstructing function 150*c*, a controlling function 150*d*, and a display controlling function 150*e*. These functions will be explained in detail later.

In an embodiment, processing functions implemented by the obtaining function 150*a*, the determining function 150*b*, the reconstructing function 150*c*, the controlling function 150*d*, and the display controlling function 150*e* are stored in the storage 130 in the form of computer-executable programs. The processing circuitry 150 is a processor configured to realize the functions corresponding to the programs by reading and executing the programs from the storage 130. In other words, the processing circuitry 150 that has read the programs has the functions illustrated within the processing circuitry 150 in FIG. 1.

Further, although the example is explained with reference to FIG. 1 in which the single piece of processing circuitry (i.e., the processing circuitry 150) realizes the processing functions implemented by the obtaining function 150*a*, the determining function 150*b*, the reconstructing function 150*c*, the controlling function 150*d*, and the display controlling function 150*e*, it is also acceptable to structure the processing circuitry 150 by combining together a plurality of independent processors so that the functions are realized as a result of the processors executing the programs. In other words, each of the abovementioned functions may be structured as a program, so that the single piece of processing circuitry (i.e., the processing circuitry 150) executes the programs. In another example, one or more specific functions may be installed in dedicated and independent program executing circuitry.

The term "processor" used in the above explanations denotes, for example, a Central Processing Unit (CPU), a Graphical Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)). The one or more processors are configured to realize the functions by reading and executing the programs saved in the storage 130.

In FIG. 1, the obtaining function 150*a*, the determining function 150*b*, the reconstructing function 150*c*, the controlling function 150*d*, and the display controlling function 150*e* are examples of an obtaining unit, a determining unit, a reconstructing unit, a controlling unit, and a display controlling unit, respectively.

By employing the controlling function 150*d* to control the gantry 1 and the console apparatus 2, the processing circuitry 150 is configured to exercise overall control on the PET apparatus 100. For example, by employing the controlling function 150*d*, the processing circuitry 150 is configured to control imaging processes of the PET apparatus 100. Further, by employing the controlling function 150*d*, the processing circuitry 150 is configured to control the table driving unit 106.

Next, a background of the embodiment will be explained. As a comparison example for understanding significance of the PET apparatus 100 according to the embodiment, FIG. 2 illustrates a configuration of a PET detector 30 that is a standard element of a conventional PET apparatus. The PET detector 30 is typically configured with a plurality of small scintillator pieces illustrated as scintillator pieces 30*a*, 30*b*, 30*c*, 31*a*, and so on. Each of the scintillator pieces 30*a*, 30*b*, 30*c*, 31*a*, and so on is typically in the shape of a quadrangular prism, for example, of which the width and the length are each 3 mm to 4 mm, while the height is approximately 20 mm.

In this situation, the front end circuitry 102 of the PET apparatus is configured to acquire light emission positions of interactions between pair annihilation gamma rays and the scintillator, by acquiring pieces of acquisition data numbered in units of the scintillator pieces. Further, the processing circuitry 150 is configured to generate a PET image by performing, while employing the reconstructing function 150*c*, an image reconstruction on the basis of the acquisition data acquired by the front end circuitry 102. For example, the front end circuitry 102 is configured to acquire light emission at a light emission point 5 as light emission data of the scintillator piece 30*a* and light emission at a light emission point 6 as light emission data of the scintillator piece 31*a*. Subsequently, by employing the reconstructing function 150*c*, the processing circuitry 150 is configured to estimate a Line of Response (LOR) 4 and generation positions of pair annihilation gamma rays, on the basis of the light emission data of the scintillator piece 30*a* and the light emission data of the scintillator piece 31*a*.

However, in the comparison example, the front end circuitry 102 recognizes the light emission positions of the interactions between the pair annihilation gamma rays and the scintillator only in an integer coordinate system, i.e., in units of the scintillator pieces. Thus, there is a theoretical limit to the level of precision in calculating the generation positions of the pair annihilation gamma rays.

Figure 3:
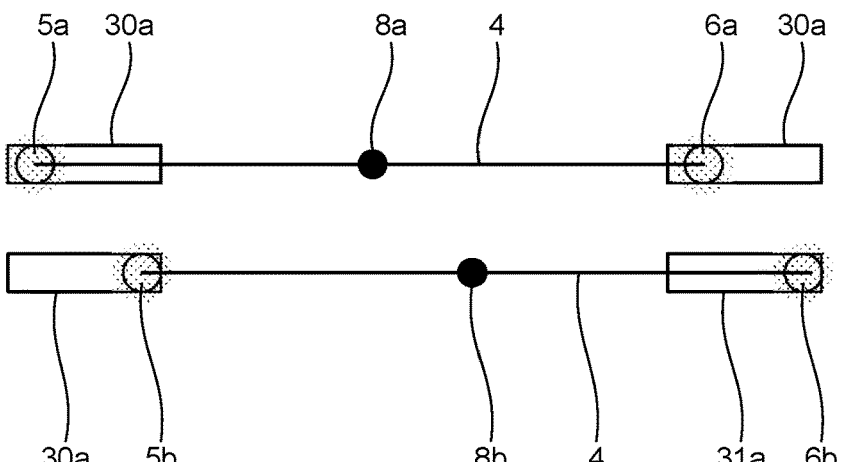
FIG. 3 is a drawing for explaining the detector included in the PET apparatus according to the comparison example.

FIG. 3 is a drawing for explaining this aspect while placing a focus on the scintillator pieces related to the light emission points in FIG. 2. For example, as illustrated in FIG. 3, when a light emission point 5*a* caused by one of the gamma rays is in a relatively deep location in the scintillator piece 30*a*, whereas a light emission point 6*a* caused by the other gamma ray is in a relatively shallow location in the scintillator piece 31*a*, the processing circuitry 150 is configured, by employing the reconstructing function 150*c*, to estimate the generation position of the pair annihilation gamma rays to be a position 8*a*. In contrast, when a light emission point 5*b* caused by one of the gamma rays is in a relatively shallow location in the scintillator piece 30*a*, whereas a light emission point 6*b* caused by the other gamma ray is in a relatively deep location in the scintillator piece 31*a*, the processing circuitry 150 is configured, by employing the reconstructing function 150*c*, to estimate the generation position of the pair annihilation gamma rays to be a position 8*b*. As explained herein, because the size of each scintillator piece is finite, there are limits to a temporal resolution 10 and a spatial resolution 11, regarding the generation positions of the pair annihilation gamma rays. These limits to the temporal resolution 10 and the spatial resolution 11 may become an obstacle in developing, for example, the PET apparatus 100 having a TOF temporal resolution of approximately 10 ps, i.e., a resolution of approximately 1.5 mm as converted into the position of a pair annihilation point.

To cope with this situation, in the PET apparatus 100 according to the embodiment, instead of performing the data processing using the integer coordinate system, i.e., in units of the scintillator pieces, the front end circuitry 102 is configured to employ the PET detector 3 using the monolithic scintillator so as to perform data acquisition implementing a Floating Edge LOR (FE-LOR) scheme based on a real number (floating point) coordinate system. In other words, according to the floating edge LOR scheme, a PET apparatus is configured to generate a LOR by connecting, to each other, two light emission points in the scintillator where the pair annihilation gamma rays became incident, instead of generating the LOR in units of the scintillator pieces.

FIG. 4 presents a conceptual drawing of the floating edge LOR scheme. From the PET detector 3 or the like including the monolithic scintillator, the front end circuitry 102 is configured to obtain the light emission points 5 of gamma rays in a real number coordinate system. In this situation, obtaining the light emission points in the real number coordinate system denotes that the front end circuitry 102 obtains the actual positions of the light emission points, instead of obtaining information indicating in which scintillator pieces the light emission occurred. Because the PET detector 3 includes the monolithic scintillator, the front end circuitry 102 is capable of obtaining the abovementioned data. By employing the reconstructing function 150*c*, the processing circuitry 150 is configured to estimate the generation positions of the gamma rays on the basis of the positions of the light emission points 5 obtained in the real number coordinate system. As described herein, the method by which the LOR is determined by obtaining the data of the light emission points in the real number coordinate system will be referred to as a floating edge method.

It should be noted that, however, to reconstruct continuous value data of the light emission points by using the floating edge LOR scheme, data processing requires ingenuity.

The present embodiments are based on the background described above. The PET apparatus 100 according to an embodiment is configured to determine virtual detector regions (explained later) and to convert data of the light emission points obtained in the real number coordinate system into data in the virtual detector regions, by projecting, onto the virtual detector regions, the data of the light emission points obtained in the real number coordinate system through a prescribed procedure. The virtual detector regions are, for example, an area element representing surfaces of virtual detectors included in the PET detector 3.

With the configuration described above, it is possible, as explained later, to perform an image reconstruction on data related to the floating edge LOR scheme, by applying an existing image reconstruction method, which is the image reconstruction method implemented on data obtained in units of the scintillator pieces, i.e., in the integer coordinate system. Accordingly, the processing circuitry 150 is able to perform the image reconstruction on the data related to the floating edge LOR scheme, by using the existing image reconstruction method for which know-how and the like have sufficiently been accumulated. Consequently, it is possible to overcome the theoretical limit to image resolutions presented by the conventional image reconstruction performed on the conventional coincidence data expressed in units of the scintillator pieces. We are therefore closer to realizing a high resolution PET apparatus.

Figure 6:
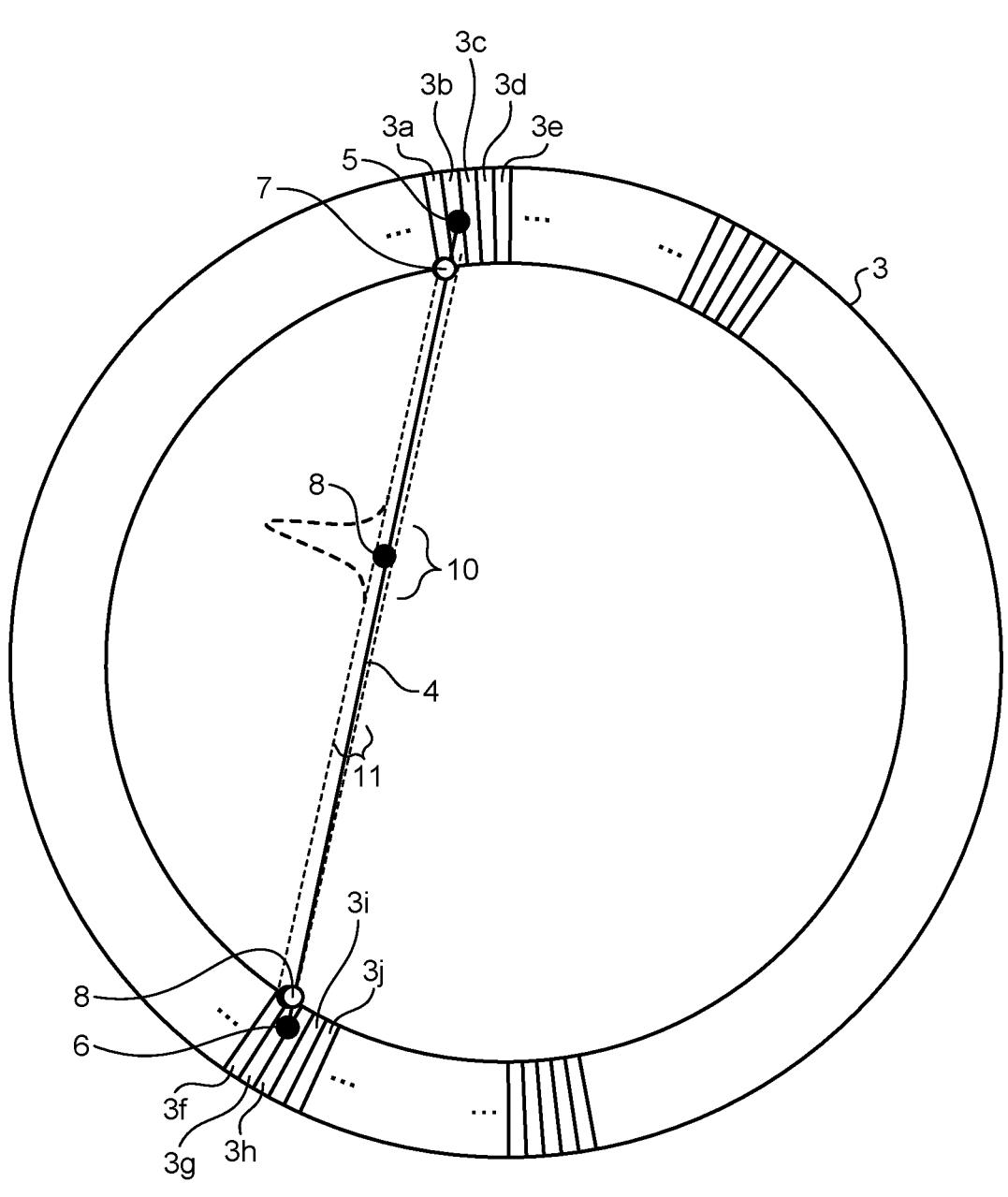
FIG. 6 is a drawing for explaining a process performed by the PET apparatus according to the first embodiment.
Figure 7:
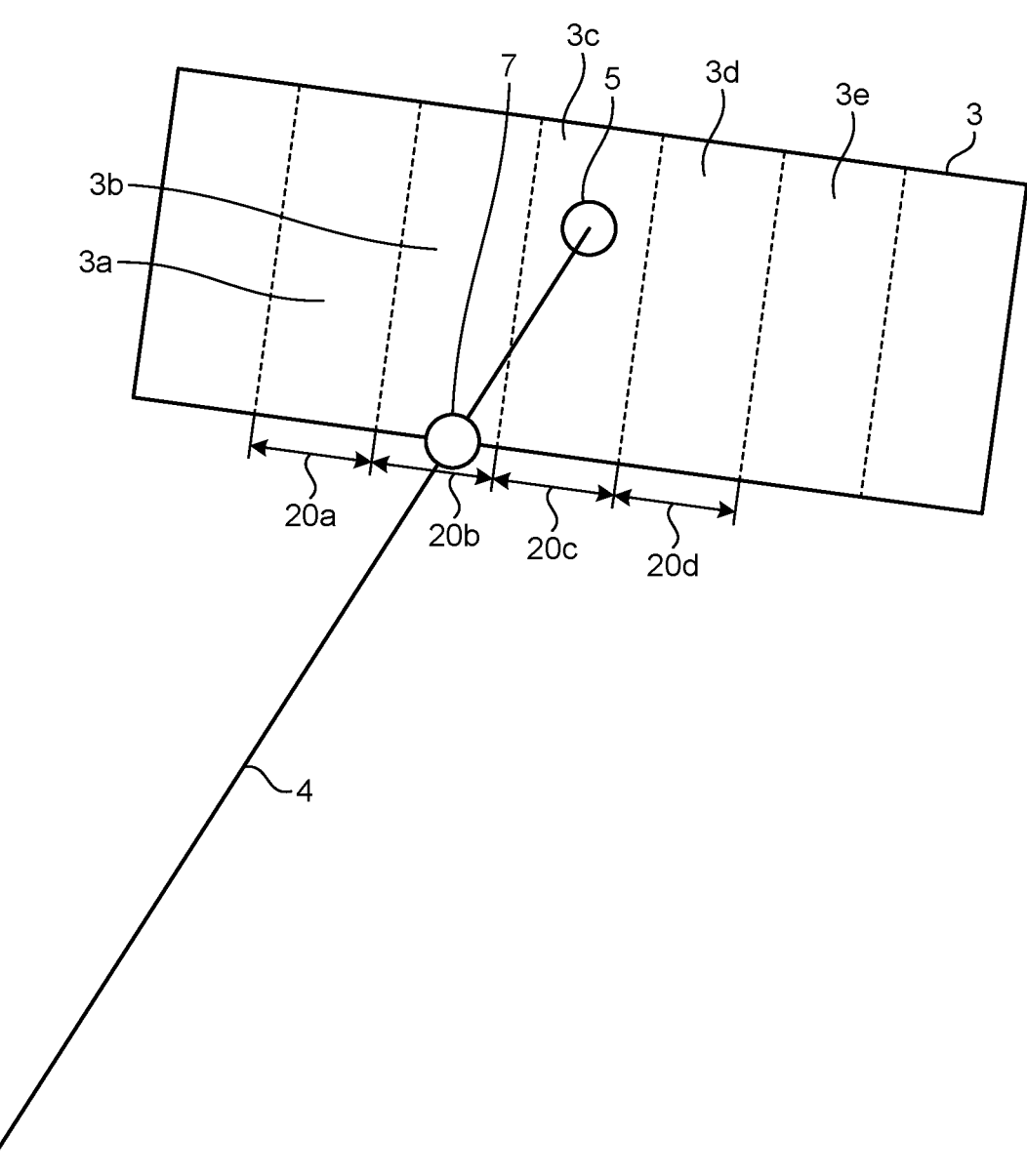
FIG. 7 is another drawing for explaining the process performed by the PET apparatus according to the first embodiment.

Next, a specific configuration of the PET apparatus 100 according to the embodiment will be explained with reference to FIGS. 5 to 7. FIG. 5 is a flowchart indicating a flow in a process performed by the PET apparatus 100 according to a first embodiment. FIG. 6 is a drawing for explaining the PET detector 3 included in the PET apparatus 100 according to the first embodiment. In the first embodiment, because the PET detector 3 included in the PET apparatus 100 is configured by using the monolithic scintillator and the like, for example, the PET detector 3 is able to obtain the data of the light emission points of the gamma rays in the real number coordinate system that is continuously expressed, instead of in units of scintillator pieces.

To simplify the explanations, with reference to FIG. 6, an example will be explained in which the PET detector 3 is configured by using the single monolithic scintillator; however, in actuality, the PET detector 3 may be configured by using a plurality of monolithic scintillators, for example. In that situation, although there would be data seams in boundary sections between any two of the plurality of monolithic scintillators, the PET detector 3 would still be able, in the other locations, to obtain the data of the light emission points of the gamma rays in the real number coordinate system that is continuously expressed. Accordingly, even in the situation where the PET detector 3 is configured by using the plurality of monolithic scintillators, the processing circuitry 150 would be able to generate a PET image by performing a similar image reconstruction process.

To begin with, at step S100, the front end circuitry 102 detects, in the real number coordinate system, light emission positions and times of events occurring due to the pair annihilation gamma rays. By employing the obtaining function 150a, the processing circuitry 150 obtains the light emission positions and the times of the events occurring due to the pair annihilation gamma rays, from the front end circuitry 102. In an example, by employing the obtaining function 150a, as illustrated in FIG. 6, the processing circuitry 150 obtains the positions of the light emission points 5 and 6 of the gamma rays and the light emission times thereof. In this situation, because the PET detector 3 is a detector including the monolithic scintillator, there are no seams between scintillator pieces, unlike the example in FIG. 3. Thus, by employing the obtaining function 150a, the processing circuitry 150 obtains the positions of the light emission points 5 and 6 of the gamma rays in the real number coordinate system that is continuously expressed, instead of in units of the scintillator pieces. In other words, the PET detector 3 is a detector capable of detecting, in the real number coordinate system, the light emission positions of the events occurring as a result of pair annihilation gamma rays becoming incident (hereinafter, "incidence of the pair annihilation gamma rays"). Further, in FIG. 6, virtual detectors 3a, 3b, 3c, 3d, 3e, 3f, 3g, 3h, 3i, 3j, and so on are virtual detectors that are set for data processing in the PET detector 3. Thus, it does not mean that the PET detector 3 is physically structured with a plurality of scintillator pieces.

Subsequently, at step S110, by employing the reconstructing function 150c, the processing circuitry 150 generates a floating edge LOR (FE-LOR) by connecting together the light emission positions of the gamma rays obtained at step S100. In other words, by employing the reconstructing function 150c, the processing circuitry 150 generates a LOR 4 serving as the floating edge LOR, by connecting together the light emission points 5 and 6 of the gamma rays obtained at step S100, with a straight line.

After that, at step S120, by employing the determining function 150b, the processing circuitry 150 divides a detector region of the PET detector 3 into a plurality of virtual detectors, for example, at least in a circumferential direction. In an example, as illustrated in FIG. 6, by employing the determining function 150b, the processing circuitry 150 divides the detector region of the PET detector 3 into the virtual detectors 3a, 3b, 3c, 3d, 3e, 3f, 3g, 3h, 3i, 3j, and so on in the circumferential direction. In this situation, by employing the determining function 150b, the processing circuitry 150 makes smaller the width of each of the virtual detectors resulting from the division than the width of each of the scintillator pieces 30a, 30b, 30c, and so on of the conventional PET apparatus 100 and is thus able to enhance the spatial resolution 11 and the temporal resolution 10 of an image to be reconstructed. By employing the determining function 150b, the processing circuitry 150 determines the width and the division number of the virtual detectors, while taking into consideration balance between a resolution required of the reconstructed image and the quantity of the events for the data acquired by the front end circuitry 102, so as to divide the detector region of the PET detector 3 into the plurality of virtual detectors on the basis of the width and the division number of the virtual detectors that were determined.

In this situation, the width and the division number or the like of the virtual detectors may be determined in advance before the start of an imaging process or may be determined on the basis of imaging data, for example, after an imaging process is started, after an imaging process is started. Further, these parameters may be changed as appropriate when necessary. In an example, the processing circuitry 150 may generate a PET image by employing the reconstructing function 150c at step S150 (explained later) and, subsequently, if it is determined that image quality can be improved by changing the virtual detector dividing method used at step S120, the process may return to step S120 so as to re-configure the parameters such as the width and the division number, or the like of the virtual detectors. In that situation, the steps illustrated in FIG. 5 will be performed again on the basis of the re-configured parameters.

Subsequently, at step S130, by employing the determining function 150b, the processing circuitry 150 determines the virtual detector regions for which the event-related data obtained at step S110 is to be converted and which serve as a basis of the reconstruction process (explained later). More specifically, in the first embodiment, by employing the determining function 150*b*, the processing circuitry 150 determines the virtual detector regions, by calculating the intersection points between curved planes representing the surfaces of the virtual detectors resulting from step S120 and the floating edge LOR. For example, in FIG. 6, by employing the determining function 150*b*, the processing circuitry 150 determines virtual detectors to which the events identified with the light emission point 5 and the light emission point 6 belong, by calculating an intersection point 7, which is the intersection point between the curved plane representing the surface of the virtual detector 3*a* being one of the virtual detectors set at step S120 and the LOR 4 serving as the floating edge LOR, so as to determine a virtual detector region.

The situation described above will be explained, with reference to FIG. 7. FIG. 7 is an enlarged view of FIG. 6. In FIG. 7, the virtual detectors 3*a*, 3*b*, 3*c*, 3*d*, and 3*e* represent the plurality of virtual detectors set with respect to the detector region of the PET detector 3 at step S120. In this situation, in the first embodiment, the planes representing the surfaces of the virtual detectors serves as the virtual detector regions. In other words, the virtual detector regions are an area element that extends two-dimensionally on the surfaces of the virtual detectors. In an example, among the faces of the virtual detectors, the faces positioned closer to the center of the ring of the PET detector 3 serve as the virtual detector regions. In other words, while a virtual curved plane surrounding the patient is imagined, the region corresponding to the surface of the PET detector 3 positioned on the patient side serves as the virtual detector regions, for example. For instance, of the surfaces of the virtual detector 3*a*, an area element that is the surface positioned closer to the center of the ring of the PET detector 3 and that extends two-dimensionally serves as a virtual detector region 20*a* corresponding to the virtual detector 3*a*. Similarly, virtual detector regions 20*b*, 20*c*, and 20*d* serve as virtual detector regions corresponding to the virtual detectors 3*b*, 3*c*, and 3*d*, respectively.

In this situation, at step S130, by employing the determining function 150*b*, the processing circuitry 150 determines, with respect to the data related to the events obtained at step S110, a virtual detector region to which each of the events belongs. In other words, by employing the determining function 150*b*, the processing circuitry 150 determines the virtual detector regions with respect to the data related to the events obtained at step S110, on the basis of the floating edge Line Of Response (LOR) defined based on the events detected by the PET detector 3 and the light emission positions of the events occurring due to the incidence of the pair annihilation gamma rays. More specifically, by employing the determining function 150*b*, the processing circuitry 150 determines the virtual detector regions to which the events detected by the PET detector 3 belong, by calculating the intersection points between the planes representing the surfaces of the virtual detectors and the floating edge LOR. For example, by employing the determining function 150*b*, the processing circuitry 150 determines, with respect to the light emission point 5, a virtual detector region to which the light emission point 5 belongs, by calculating the intersection point 7 between a plane representing the surfaces of the virtual detectors 3*a* to 3*d* and the LOR 4 serving as the floating edge LOR. In the example in FIG. 7, by employing the determining function 150*b*, the processing circuitry 150 determines, with respect to the light emission point 5, the virtual detector region 20*b* which is the surface of the virtual detector 3*b* and to which the intersection point 7 belongs, as the virtual detector region to which the light emission point

5 belongs. Similarly, by employing the determining function 150*b*, the processing circuitry 150 determines, with respect to the light emission point 6 in FIG. 6, a virtual detector region to which the light emission point 6 belongs, by calculating an intersection point 8 between a plane representing the surfaces of the virtual detectors 3*f* to 3*j* and the LOR 4 serving as the floating edge LOR. In other words, by employing the determining function 150*b*, the processing circuitry 150 determines, with respect to the light emission point 6, the virtual detector region to which the intersection point 8 belongs, as the virtual detector region to which the light emission point 6 belongs.

Subsequently, at step S140, by employing the determining function 150*b*, the processing circuitry 150 calculates, with respect to the data related to each of the events obtained at step S110, a virtual light emission point (an incidence point) which is a light emission point based on the assumption that the light emission occurred in the virtual detector region and a virtual incidence time which is an incidence time based on the assumption that the event in the light emission position occurred at the virtual light emission point. To begin with, by employing the determining function 150*b*, the processing circuitry 150 calculates the intersection points determined at step S130, i.e., the intersection points between the planes representing the surfaces of the virtual detectors and the LOR, as virtual light emission points. For example, by employing the determining function 150*b*, the processing circuitry 150 calculates, with respect to the light emission point 5, the intersection point 7 being the intersection point between the virtual detector region 20*b* serving as the plane representing the surface of the virtual detector 3*b* and the LOR 4, as a virtual light emission point which is a light emission point based on the assumption that the light emission related to the light emission point 5 occurred in the virtual detector region 20*b*. Similarly, by employing the determining function 150*b*, the processing circuitry 150 calculates, with respect to the light emission point 6, the intersection point 8 between the virtual detector region serving as the plane representing the surface of the virtual detector 3*g* and the LOR 4, as a virtual light emission point corresponding to the light emission point 6.

After that, by employing the determining function 150*b*, the processing circuitry 150 calculates the virtual incidence time, which is an incidence time based on the assumption that the event occurred at the virtual light emission point. More specifically, by employing the determining function 150*b*, the processing circuitry 150 calculates the distance between the actual light emission point and the virtual light emission point. For instance, in the example of FIG. 7, by employing the determining function 150*b*, the processing circuitry 150 calculates the distance between the light emission point 5 being the actual light emission point and the intersection point 7 being the virtual light emission point. Subsequently, by employing the determining function 150*b*, the processing circuitry 150 calculates a delay time period indicating the time required for a gamma ray present at the virtual light emission point at a certain time to arrive at the actual light emission point, by dividing the calculated distance by the speed of light. After that, by employing the determining function 150*b*, the processing circuitry 150 calculates the virtual incidence time which is an incidence time based on the assumption that the event at the light emission point 5 occurred at the intersection point 7 serving as the virtual light emission point, by subtracting the calculated delay time period from the time at which the light emission was observed at the actual light emission point. Similarly, by employing the determining function 150*b*, the processing circuitry 150 calculates a virtual incidence time based on the assumption that the event at the light emission point 6 occurred at the intersection point 8 serving as the virtual light emission point.

With the steps described above, the data at the times when the actual light emission occurred at the light emission point 5 and at the light emission point 6 obtained in the real number coordinate system has been converted into the data at the virtual light emission times at the intersection point 7 serving as the virtual light emission point and at the intersection point 8 serving as the virtual light emission point in the virtual detector regions. In other words, the problem regarding the image reconstruction with the floating edge LOR of the PET detector 3 including the monolithic scintillator has been reduced to a problem of an image reconstruction by a conventional PET detector structured with the plurality of scintillator pieces arranged on the surface of the PET detector 3.

At step S150, by employing the reconstructing function 150*c*, the processing circuitry 150 performs a PET image reconstruction process, by using an existing image reconstruction algorithm, on the basis of the virtual light emission points and the virtual incidence times calculated at step S140. In other words, by employing the reconstructing function 150*c*, the processing circuitry 150 performs the PET image reconstruction process by using the existing image reconstruction algorithm, on the basis of the virtual detector regions determined at step S130 and coincidence information including the virtual light emission points and the virtual incidence times calculated at step S140.

Further, in another example, at step S150, the processing circuitry 150 may further divide the virtual detector regions into sections so as to consider each of the virtual detector region sections resulting from the division as a virtual scintillator piece, and may acquire coincidence information by discretely expressing the virtual light emission points, so as to perform a PET image reconstruction process by employing the reconstructing function 150*c* on the basis of the acquired coincidence information.

As explained above, according to the first embodiment, by employing the PET detector 3 including the monolithic scintillator, the PET apparatus 100 is configured to obtain, in the real number coordinate system, the light emission positions and the times of the events occurring due to the incidence of the pair annihilation gamma rays and to determine the virtual detector regions by dividing the detector region of the PET detector 3 into the plurality of virtual detectors. Subsequently, the PET apparatus 100 is configured to convert the light emission positions and the times that were obtained, into the virtual light emission points and the virtual incidence times in the virtual detector regions. As a result, when performing the image reconstruction implementing the floating edge LOR scheme, the PET apparatus 100 according to the embodiment is able to make use of the image reconstruction algorithm and the know-how of the image reconstruction method used by conventional PET apparatuses. It is therefore possible to aim at realizing a PET apparatus having a higher resolution, such as a 10-ps PET apparatus, for example.

Second Embodiment

In the first embodiment, the example was explained in which the detector region of the PET detector 3 is divided into the plurality of virtual detectors in the circumferential direction, so as to determine the virtual detector regions that extend two-dimensionally. However, possible embodiments are not limited to this example. By employing the determining function 150*b*, the processing circuitry 150 may divide the region of the PET detector 3 into a plurality of virtual detectors, three-dimensionally including not only the circumferential direction, but also a radial direction. In other words, in a second embodiment, virtual detector regions determined by the processing circuitry 150 while employing the determining function 150*b* are a volume element that extends three-dimensionally. The PET apparatus 100 according to the second embodiment can be considered as a virtual detector PET apparatus of a Depth-Of-Interaction (DOI) type that is divided into the plurality of virtual detectors by using virtual volume pieces extending three-dimensionally. It is therefore possible to perform an image reconstruction while using an image reconstruction algorithm of a DOI-type PET apparatus.

FIG. 8 presents a flowchart for explaining a flow in a process performed by the PET apparatus 100 according to the second embodiment. The processes other than those at steps S120A and S130A are the same as the processes in the first embodiment. Thus, explanations of the duplicate parts of the processes that are the same as those in the first embodiment will be omitted.

To begin with, at step S100, the front end circuitry 102 detects, in the real number coordinate system, the light emission positions and the times of the events occurring due to the pair annihilation gamma rays. Subsequently, at step S110, by employing the reconstructing function 150*c*, the processing circuitry 150 generates a Floating Edge LOR (FE-LOR) by connecting together the light emission positions of the gamma rays obtained at step S100.

At step S120A, by employing the determining function 150*b*, the processing circuitry 150 divides the detector region of the PET detector 3 into a plurality of virtual detectors. In this situation, although in the first embodiment, the example was explained in which the processing circuitry 150 divides the detector region of the PET detector 3 in the circumferential direction by employing the determining function 150*b*, in the second embodiment, the detector region is additionally divided into a plurality of virtual detectors in the radial direction of the ring of the PET detector 3, i.e., in a depth direction. In other words, by employing the determining function 150*b*, the processing circuitry 150 divides the region of the PET detector 3 into the plurality of virtual detectors at least in the circumferential direction and the radial direction.

Figure 9:
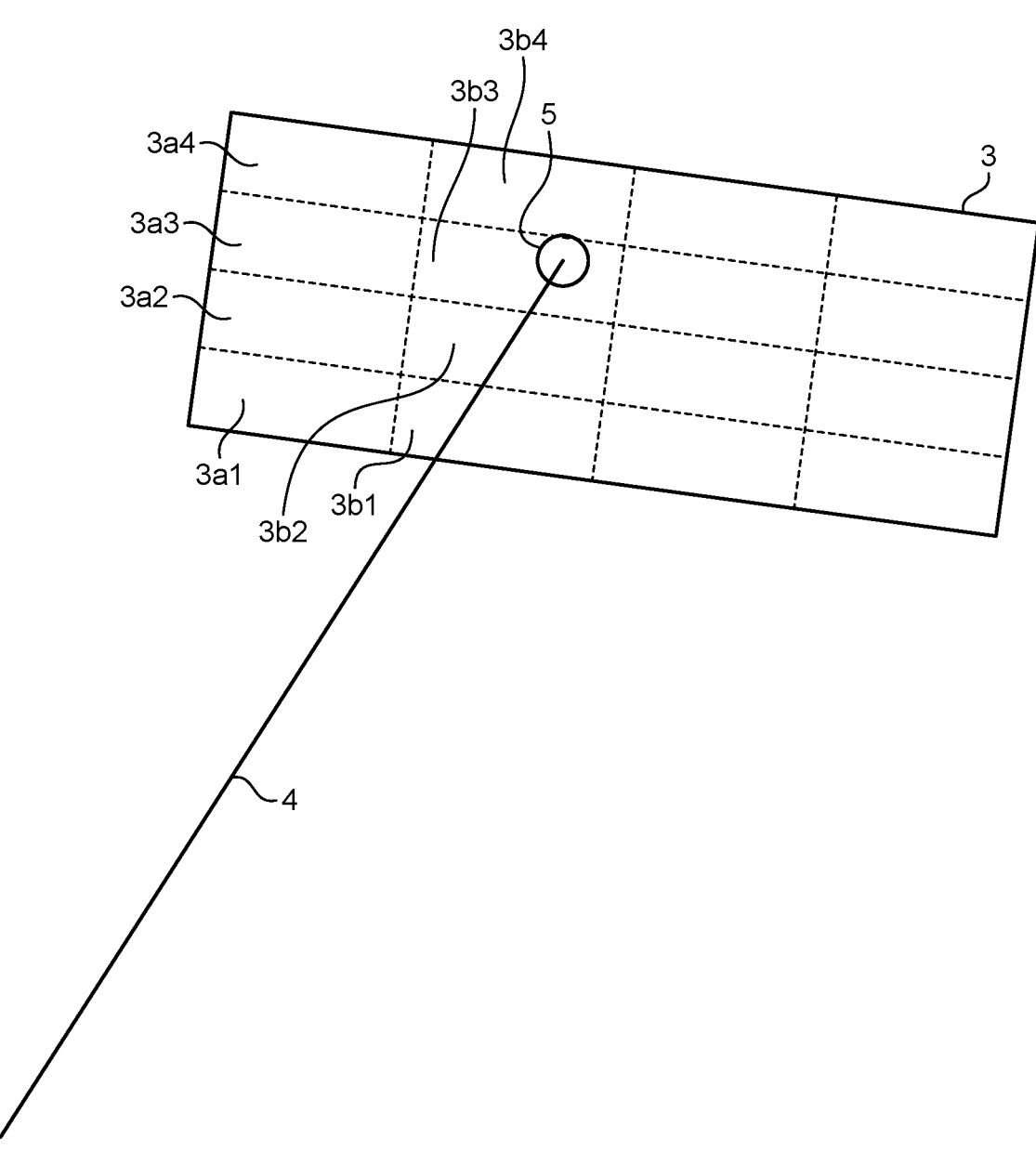
FIG. 9 is a drawing for explaining a process performed by the PET apparatus according to the second embodiment.

FIG. 9 illustrates an example of the dividing process. FIG. 9 is an enlarged view of the PET detector 3 illustrated in FIG. 6. In this situation, by employing the determining function 150*b*, the processing circuitry 150 divides the detector region of the PET detector 3 in the circumferential direction as well as in the radial direction (in the up-and-down direction in FIG. 9), so as to three-dimensionally divide the detector region of the PET detector 3 into small pieces such as virtual detectors 3*a*1, 3*a*2, 3*a*3, 3*a*4, 3*b*1, 3*b*2, 3*b*3, 3*b*4, and so on. Because the detector region of the PET detector 3 is three-dimensionally divided into the small pieces, the image reconstruction performed by the PET apparatus 100 can be considered as an image reconstruction performed by a virtual detector PET apparatus of the DOI type. At step S150, by using a reconstruction algorithm used by the virtual detector PET apparatus of the DOI type, the processing circuitry 150 is able to perform an image reconstruction related to the floating edge LOR. Further, because the pieces of the virtual detectors resulting from the division are smaller, it is possible to enhance the spatial resolution 11 and the temporal resolution 10 to be reconstructed.

Subsequently, at step S130A, by employing the determining function 150b, the processing circuitry 150 determines virtual detector regions. In this situation, in the second embodiment, the virtual detector regions are a volume element that extends three-dimensionally, while the region inside each of the plurality of virtual detectors resulting from the three-dimensional division serves as a virtual detector region. In other words, by employing the determining function 150b, the processing circuitry 150 determines the virtual detector regions to which the events occurring due to the incidence of the pair annihilation gamma rays belong, by determining to which virtual detector each of the light emission positions of the events occurring due to the incidence of the pair annihilation gamma rays belongs. For example, in FIG. 9, by employing the determining function 150b, the processing circuitry 150 determines, with respect to the light emission point 5, the region of the virtual detector 3b3 including the light emission point 5, as a virtual detector region. Similarly, by employing the determining function 150b, the processing circuitry 150 determines, with respect to the light emission point 6, the region of the virtual detector including the light emission point 6, as a virtual detector region.

After that, at step S140, by employing the determining function 150b, the processing circuitry 150 calculates virtual light emission points and virtual incidence times. In an example, by employing the determining function 150b, the processing circuitry 150 calculates the center coordinates of a virtual detector corresponding to the virtual detector region associated with each of the light emission points, as a virtual light emission point. Further, by employing the determining function 150b, the processing circuitry 150 calculates the distances between the virtual light emission points and the light emission points, so as to calculate the virtual incidence times on the basis of the calculated distances and the light emission times acquired at step S100.

Subsequently, at step S150, by employing the reconstructing function 150c, the processing circuitry 150 performs a PET image reconstruction process by using an existing image reconstruction algorithm, on the basis of the virtual light emission points and the virtual incidence times calculated at step S140. In particular, by employing the reconstructing function 150c, the processing circuitry 150 performs the PET image reconstruction process by using the existing image reconstruction algorithm used by a PET apparatus of the DOI type, on the basis of coincidence information including the virtual detector regions determined at step S130A, as well as the virtual light emission points and the virtual incidence times calculated at step S140.

As explained above, in the second embodiment, the PET apparatus 100 is configured to perform the process by three-dimensionally dividing the detector region of the PET detector 3. Consequently, it is possible to perform the image reconstruction related to the floating edge LOR by using the image reconstruction algorithm used by the PET apparatus of the DOI type.

Other Embodiments

Possible embodiments are not limited to the above examples. It is also acceptable to perform an image reconstruction related to the floating edge LOR by using other methods.

In a first example, it is also acceptable to perform an image reconstruction by directly performing a reconstruction process on the data obtained in the real number coordinate system, without discretizing the data obtained in the real number coordinate system at step S100. In other words, by employing the reconstructing function 150c, the processing circuitry 150 may reconstruct a PET image by plotting, on the floating edge LOR connecting the pair annihilation point coordinates to each other obtained at step S110, pair annihilation points of the gamma rays obtained from TOF information.

In a second example, an image reconstruction related to the floating edge LOR may be performed by expanding a system matrix into continuous values, although system matrices are usually handled while being discretized. In other words, by employing the reconstructing function 150c, the processing circuitry 150 may perform the image reconstruction on the basis of: the system matrix that is expanded to the continuous values and that expresses a transition probability from the pair annihilation point coordinates to the floating edge LOR; and data related to the light emission positions and the times of the events occurring due to the incidence of the pair annihilation gamma rays obtained in the real number coordinate system at step S100.

Further, in a third example, an image reconstruction may be performed by using a deep learning model. In other words, by employing the reconstructing function 150c, the processing circuitry 150 may perform an image reconstruction of a PET image, on the basis of the deep learning model using the floating edge LOR generated at step S110 and the TOF information.

As for these reconstruction methods, the pair annihilation positions may be calculated as continuous values (real number values) up to the stage where the pair annihilation points are calculated, so that a final image is generated by rounding those values in correspondence with pixels at the stage of generating the final image. In other words, by employing the reconstructing function 150c, the processing circuitry 150 may calculate a pixel expression of the reconstructed image, by re-sampling a pair annihilation point distribution that is expressed with real number coordinates, i.e., with pixels in a sufficiently small size and that is obtained from the reconstruction according to the first and the second embodiments and the first to the third examples above.

According to at least one aspect of the embodiments described above, it is possible to perform the image reconstruction with respect to the floating edge LOR.

In relation to the embodiments described above, the following notes are presented as a number of aspects and selected characteristics of the present disclosure:

Note 1:

A Positron Emission Tomography (PET) apparatus provided in one aspect of the present disclosure includes a Positron Emission Tomography (PET) detector, a determining unit, and a reconstructing unit. The PET detector is capable of detecting, in a real number coordinate system, a light emission position of an event occurring due to pair annihilation gamma rays becoming incident. The determining unit is configured to determine a virtual detector region on the basis of a Line Of Response (LOR) defined based on the event detected by the PET detector and the light emission position. The reconstructing unit is configured to perform a reconstruction process on the basis of the virtual detector region.

Note 2:

The PET detector may be a detector including a monolithic scintillator.

Note 3:

The virtual detector region may be an area element.

Note 4:

The determining unit may be configured:

to divide a region of the PET detector into a plurality of virtual detectors at least in a circumferential direction; and to determine the virtual detector region to which the event belongs, by calculating an intersection point between a plane representing surfaces of the virtual detectors and the LOR.

Note 5:

The determining unit may be configured to determine a width or a division number of the virtual detector, on the basis of a resolution required of a reconstructed image.

Note 6:

The determining unit may be configured to re-configure the width or the division number of the virtual detector after reconstructing a PET image.

Note 7:

The determining unit may be configured:

to calculate the intersection point between the plane representing the surfaces of the virtual detectors and the LOR as a virtual light emission point; and to calculate, on the basis of the virtual light emission point and the light emission position, a virtual incidence time being an incidence time based on an assumption that the event at the light emission position occurred at the virtual light emission point.

Note 8:

The determining unit may be configured: to calculate the distance between a light emission point and the virtual light emission point; to calculate a delay time period indicating the time required for a gamma ray present at the virtual light emission point at a certain time to arrive at an actual light emission point, by dividing the calculated distance by the speed of light; and to calculate the virtual incidence time by subtracting the calculated delay time period from a time at which light emission is observed at the light emission point.

Note 9:

The determining unit may be configured to convert data of a light emission point obtained in the real number coordinate system into data in the virtual detector region, by projecting the data of the light emission point obtained in the real number coordinate system, onto the virtual detector region through a prescribed procedure.

Note 10:

The reconstructing unit may be configured to perform the reconstruction process on the basis of the virtual light emission point and the virtual incidence time.

Note 11:

Among the faces of the virtual detectors, the plane may represent faces positioned closer to the center of a ring of the PET detector.

Note 12:

The virtual detector region may be a region of the surface of the PET detector positioned on the side of an imaged subject.

Note 13:

The determining unit may be configured: to further divide the virtual detector region into sections; and to determine each of the sections into which the virtual detector region has been divided, as a virtual scintillator piece.

Note 14:

The virtual detector region may be a volume element.

Note 15:

The determining unit may be configured:

to divide the region of the PET detector into a plurality of virtual detectors at least in the circumferential direction and a radial direction; and to determine the virtual detector region to which the event belongs, by determining which of the virtual detectors the light emission position belongs.

Note 16:

The reconstructing unit may be configured to reconstruct a PET image by plotting, on a floating edge LOR connecting pair annihilation point coordinates to each other, pair annihilation points of gamma rays obtained from TOF information.

Note 17:

The reconstructing unit may be configured to perform an image reconstruction, on the basis of: a system matrix that is expanded to continuous values and that expresses a transition probability from pair annihilation point coordinates to the floating edge LOR; and data related to the light emission position and a time of the event.

Note 18:

The reconstructing unit may be configured to perform an image reconstruction of a PET image, on the basis of a deep learning model using the floating edge LOR and the TOF information.

Note 19:

The reconstructing unit may be configured to calculate a pixel expression of a reconstructed image, by re-sampling a pair annihilation point distribution obtained from a reconstruction process.

Note 20:

An image processing method provided in another aspect of the present disclosure includes:

determining a virtual detector region on the basis of a Line Of Response (LOR) defined based on an event detected by a Positron Emission Tomography (PET) detector and a light emission position, the PET detector being capable of detecting, in a real number coordinate system, the light emission position of the event occurring due to pair annihilation gamma rays becoming incident; and performing a reconstruction process on the basis of the virtual detector region.

Note 21:

A program provided in yet another aspect of the present disclosure is configured to cause a computer to execute:

determining a virtual detector region on the basis of a Line Of Response (LOR) defined based on an event detected by a Positron Emission Tomography (PET) detector and a light emission position, the PET detector being capable of detecting, in a real number coordinate system, the light emission position of the event occurring due to pair annihilation gamma rays becoming incident; and performing a reconstruction process on the basis of the virtual detector region.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A Positron Emission Tomography (PET) apparatus, comprising:

a Positron Emission Tomography (PET) detector configured to detect, in a real number coordinate system, a light emission position of an event occurring due to pair annihilation gamma rays becoming incident; and processing circuitry configured to:

determine a virtual detector region based on the PET detector, a Line Of Response (LOR) defined based on the event detected by the PET detector, and the light emission position; and perform a reconstruction process based on the determined virtual detector region, wherein the virtual detector region is an area element, the processing circuitry is further configured to divide a region of the PET detector into a plurality of virtual detectors at least in a circumferential direction, and determine the virtual detector region to which the event belongs by calculating an intersection point between a plane representing surfaces of the virtual detectors and the LOR, and the processing circuitry is further configured to calculate the intersection point between the plane representing the surfaces of the virtual detectors and the LOR as a virtual light emission point;

calculate, based on the virtual light emission point and the light emission position, a virtual incidence time being an incidence time based on an assumption that the event at the light emission position occurred at the virtual light emission point; and perform the reconstruction process based on the virtual light emission point and the virtual incidence time.

2. The PET apparatus according to claim 1, wherein the PET detector is a detector including a monolithic scintillator.

3. The PET apparatus according to claim 1, wherein, among faces of the virtual detectors, the plane represents faces positioned closer to a center of a ring of the PET detector.

4. A Positron Emission Tomography (PET) apparatus, comprising:

a Positron Emission Tomography (PET) detector configured to detect, in a real number coordinate system, a light emission position of an event occurring due to pair annihilation gamma rays becoming incident; and processing circuitry configured to determine a virtual detector region based on the PET detector, a Line Of Response (LOR) defined based on the event detected by the PET detector, and the light emission position; and perform a reconstruction process based on the virtual detector region, wherein the virtual detector region is a volume element, and the processing circuitry is further configured to divide the region of the PET detector into a plurality of virtual detectors at least in a circumferential direction and a radial direction; and determine the virtual detector region to which the event belongs, by determining which of the virtual detectors the light emission position belongs.

5. An image processing method, comprising:

determining a virtual detector region based on a Line Of Response (LOR) defined based on an event detected by a Positron Emission Tomography (PET) detector and a light emission position, the PET detector being configured to detect, in a real number coordinate system, the light emission position of the event occurring due to pair annihilation gamma rays becoming incident; and performing a reconstruction process based on the virtual detector region, wherein the virtual detector region is an area element and the method further comprises dividing a region of the PET detector into a plurality of virtual detectors at least in a circumferential direction, and determining the virtual detector region to which the event belongs by calculating an intersection point between a plane representing surfaces of the virtual detectors and the LOR, and the method further comprises calculating the intersection point between the plane representing the surfaces of the virtual detectors and the LOR as a virtual light emission point;

calculating, based on the virtual light emission point and the light emission position, a virtual incidence time being an incidence time based on an assumption that the event at the light emission position occurred at the virtual light emission point; and performing the reconstruction process based on the virtual light emission point and the virtual incidence time.

6. A non-transitory computer-readable storage medium comprising instructions that cause a computer to execute:

determining a virtual detector region based on a Line Of Response (LOR) defined based on an event detected by a Positron Emission Tomography (PET) detector and a light emission position, the PET detector being configured to detect, in a real number coordinate system, the light emission position of the event occurring due to pair annihilation gamma rays becoming incident; and performing a reconstruction process based on the virtual detector region, wherein the virtual detector region is an area element, the non-transitory computer-readable storage medium further comprises instructions that cause the computer to execute:

dividing a region of the PET detector into a plurality of virtual detectors at least in a circumferential direction, and determining the virtual detector region to which the event belongs by calculating an intersection point between a plane representing surfaces of the virtual detectors and the LOR, and the non-transitory computer-readable storage medium further comprises instructions that cause the computer to execute:

calculating the intersection point between the plane representing the surfaces of the virtual detectors and the LOR as a virtual light emission point;

calculating, based on the virtual light emission point and the light emission position, a virtual incidence time being an incidence time based on an assumption that the event at the light emission position occurred at the virtual light emission point; and performing the reconstruction process based on the virtual light emission point and the virtual incidence time.

* * * * *